United States Patent
McGuckin, Jr.

(10) Patent No.: US 10,376,400 B2
(45) Date of Patent: Aug. 13, 2019

(54) GASTRIC BYPASS SYSTEM AND METHOD

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

(*) Notice: Subject to any disclaimer, the term of this patent is extended or adjusted under 35 U.S.C. 154(b) by 650 days.

(21) Appl. No.: 14/859,280

(22) Filed: Sep. 19, 2015

(65) Prior Publication Data

US 2016/0100971 A1    Apr. 14, 2016

Related U.S. Application Data

(60) Provisional application No. 62/062,366, filed on Oct. 10, 2014.

(51) Int. Cl.
  *A61F 2/04* (2013.01)
  *A61F 5/00* (2006.01)
  *A61B 17/11* (2006.01)

(52) U.S. Cl.
  CPC ........ *A61F 5/0076* (2013.01); *A61B 17/1114* (2013.01); *A61F 2/04* (2013.01); *A61F 5/0089* (2013.01); *A61B 2017/1139* (2013.01); *A61F 2002/045* (2013.01)

(58) Field of Classification Search
  CPC ........ A61F 5/0076; A61F 2/04; A61F 5/0089; A61F 2002/045; A61B 17/1114; A61B 2017/1139
  See application file for complete search history.

(56) References Cited

U.S. PATENT DOCUMENTS

| | | | |
|---|---|---|---|
| 2009/0227866 A1 | 9/2009 | Nakazato et al. | |
| 2013/0253550 A1* | 9/2013 | Beisel | A61B 17/1114 606/153 |
| 2014/0236064 A1* | 8/2014 | Binmoeller | A61F 5/0076 604/8 |

FOREIGN PATENT DOCUMENTS

| | | |
|---|---|---|
| WO | WO 03/097124 | 11/2003 |
| WO | WO 2012/007047 | 1/2012 |
| WO | WO 2013/009886 | 1/2013 |

OTHER PUBLICATIONS

Rosenberger LH, Yinin Hu, Zequan Yang, and Robert G. Sawyer. "Gastropexy Using the Carter-Thomason Device in Lieu of TFasteners in a Critically Ill, Severely Obese Patient: An Innovative Technique." Surg Laparosc Endosc Percutan Tech. Oct. 2012; 22(5).*

The Extended European Search Report Application No. 15187989.7 dated Apr. 4, 2016.

* cited by examiner

*Primary Examiner* — Leslie R Deak
(74) *Attorney, Agent, or Firm* — Neil D. Gershon

(57) ABSTRACT

A system and method for treating obesity including a first instrument containing a first magnet therein, the first instrument insertable into a stomach of a patient and the first magnet deployable into the stomach of the patient and having a first space. A second instrument contains a second magnet therein, the second instrument insertable into a bowel of a patient and the second magnet deployable into the bowel of the patient and having a second space. A stent is insertable into the first and second spaces to maintain an opening formed between the stomach and bowel.

17 Claims, 20 Drawing Sheets

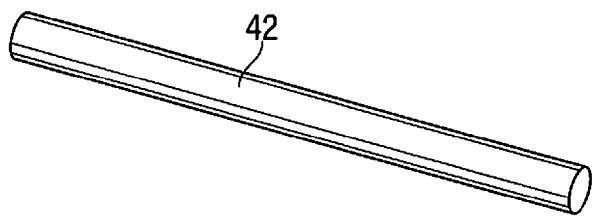
FIG. 4
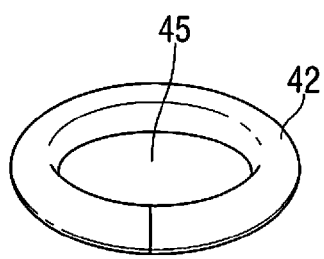 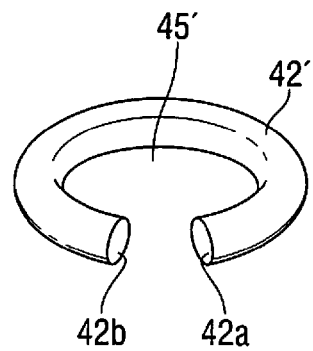
FIG. 5A          FIG. 5B

GASTRIC BYPASS SYSTEM AND METHOD

This application claims priority from provisional application Ser. No. 62/062,366, filed Oct. 10, 2014, the entire contents of which are incorporated herein by reference.

BACKGROUND OF THE INVENTION

1. Field of the Invention

The application relates to system and method treating obesity, and, more particularly, to a system and method for performing gastric bypass.

2. Background of the Related Art

The incidence of obesity continues to increase worldwide. Obesity has been defined in terms of a body mass index greater than 30, with body mass index defined by weight in kilograms divided by the square of the height in meters. (Overweight is defined as a body mass index of over 25). Obesity can cause a number of serious health conditions such as hypertension, diabetes, certain forms of cancer, coronary artery disease, stroke, congestive heart failure, and venous disease. Obesity can also cause orthopedic problems, skin problems and respiratory difficulties.

A variety of methods are currently being utilized to treat obesity. In general, these procedures fall into two categories: procedures which restrict food intake or procedures which alter the anatomy of the small intestine or divert the peristalsis of a person's food intake past the small intestine to decrease caloric absorption.

Some methods are designed to reduce the stomach by partition or bypass such as by stapling or tying off portions of the large or small intestine or stomach to reduce the amount of food desired by the patient, and the amount absorbed by the intestinal tract. In gastric banding, an adjustable band is placed externally of the stomach to constrict a portion of the stomach. Such treatments are designed to reduce the caloric intake of the individual by more rapidly triggering the satiety impulse or limiting the amount of food the individual can ingest. Complications can occur as the individual, due to the stomach restriction, may not be intaking sufficient nutrients.

Laparoscopic methods of banding and vertical banded gastroplasty have been developed, which although provide the advantages of minimally invasive surgery compared to open surgery such as less trauma, less hospital stay and faster recovery, are complicated to perform.

The need exists for an improved system and method for treating obesity.

SUMMARY OF THE INVENTION

The present invention advantageously provides a minimally invasive system and method for treating obesity.

In accordance with a first aspect, the present invention provides a method for treating obesity comprising the steps of:

inserting first and second endoscopes, the first endoscope inserted into a stomach of the patient and the second endoscope inserted into a bowel of a patient;

delivering a penetrating device to penetrate a wall of the stomach and a wall of the bowel;

approximating the bowel and stomach;

deploying a first magnet in the stomach and a second magnet in the bowel;

creating an opening between the stomach and bowel; and positioning a stent into the opening.

In some embodiments, the step of inserting a first endoscope into the stomach includes advancing the first endoscope transorally into the stomach.

In some embodiments, the method further includes the step of inserting a T-bar through the wall of the stomach and wall of the bowel and the step of approximating the bowel and stomach includes the step of pulling the T-bar proximally.

In some embodiments, the first magnet is deployed from the first endoscope and the second magnet is deployed from the second endoscope. In some embodiments, the first magnet has a first opening and the second magnet has a second opening, and the step of creating an opening between the stomach and the bowel includes inserting a cutting instrument through the first and second openings of the magnets. In some embodiments, the first magnet is retained in the first endoscope in a substantially linear position and/or the second magnet is retained in the second endoscope in a substantially linear position and the first and/or second magnets move to a curved placement position after deployment from the respective endoscope.

In some embodiments, the first endoscope has a first channel to receive the first magnet and a second channel to receive a device for approximating the stomach and bowel, and the step of deploying the first magnet advances the first magnet from the first channel. The first endoscope can have in some embodiments a third channel to receive the stent and the step of positioning the stent in the opening can include the step of advancing the stent from the third channel.

The method can include the step of removing the first and second endoscopes and closing off a portion of the stomach.

In accordance with another aspect of the present invention, a system for treating obesity is provided comprising a first instrument containing a first magnet therein, the first instrument insertable into a stomach of a patient and the first magnet deployable into the stomach of the patient and having a first space. A second instrument contains a second magnet therein, the second instrument insertable into a bowel of a patient and the second magnet deployable into the bowel of the patient and having a second space. A stent is insertable into the first and second spaces to maintain an opening formed between the stomach and bowel.

In some embodiments, the first magnet is retained in the first instrument in a substantially linear position in the delivery configuration and has a curved placement configuration after deployment from the first instrument. In some embodiments, the second magnet is retained in the second instrument in a substantially linear position in the delivery configuration and has a curved placement configuration after deployment from the second instrument.

In some embodiments, the stent has a first collapsed configuration when positioned in the first instrument and an expanded second position after exposure from the first instrument.

In some embodiments, the first instrument has a first channel to receive the first magnet and a second channel to receive a device for approximating the stomach and bowel. In some embodiments, the first instrument has a third channel to receive the stent.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 4 is a perspective view of one of the magnets of the present invention in the elongated delivery configuration;

FIG. 5A is a perspective view of the magnet of FIG. 4 in a circular placement configuration;

FIG. 5B is a perspective view of the magnet of FIG. 4 in an alternate C-shaped placement configuration;

FIGS. 6-20 illustrate the method of use of the system of the present invention wherein FIG. 6 illustrates the second endoscopic instrument being inserted into the bowel;

FIG. 7 illustrates the first endoscopic instrument being inserted into the stomach via a transoral approach;

FIG. 8 illustrates a needle and T-bar delivery sheath being advanced from the first endoscopic instrument of FIG. 1 and further showing the second endoscopic instrument positioned in the bowel;

FIG. 9 is a view similar to FIG. 8 showing the needle advanced from the delivery sheath to puncture the stomach wall;

FIG. 10 is a view similar to FIG. 9 illustrating the needle and T-bar inserted through the stomach wall and into the bowel;

FIG. 11 is a view similar to FIG. 10 showing movement of the T-bar proximally to approximate the stomach and bowel walls, and further showing initial deployment of the sheath containing the first magnet;

FIG. 12 is a view similar to FIG. 11 showing initial deployment of the first magnet from the sheath;

FIG. 13 is a view similar to FIG. 12 showing the first magnet fully released from the first endoscopic instrument and positioned in the stomach, and further showing initial deployment from the second endoscopic instrument the second sheath containing the second magnet;

FIG. 14 is a view similar to FIG. 13 showing initial deployment of the second magnet from the sheath;

FIG. 15 is a view similar to FIG. 14 showing the second magnet fully released from the second endoscopic instrument and positioned in the bowel adjacent the bowel wall and the attraction of the second and first magnets to maintain the approximated position of the stomach and bowel walls;

FIG. 16 is a view similar to FIG. 15 illustrating a puncturing device advanced from the first endoscopic instrument and being inserted through the space (opening) in the first magnet;

FIG. 17 is a view similar to FIG. 16 showing initial deployment of a sheath containing a stent from the first endoscopic instrument;

FIG. 18 is a view similar to FIG. 17 illustrating advancement of the stent sheath through the openings in the magnets;

FIG. 19 is a view similar to FIG. 18 illustrating placement of the stent in the space between the first and second magnets to maintain the opening between the stomach and bowel, and further showing the first and second endoscopic instruments being withdrawn; and FIG. 20 illustrates the stent positioned in the stomach and bowel and the endoscopic instruments removed.

DETAILED DESCRIPTION OF PREFERRED EMBODIMENTS

Figure 1:
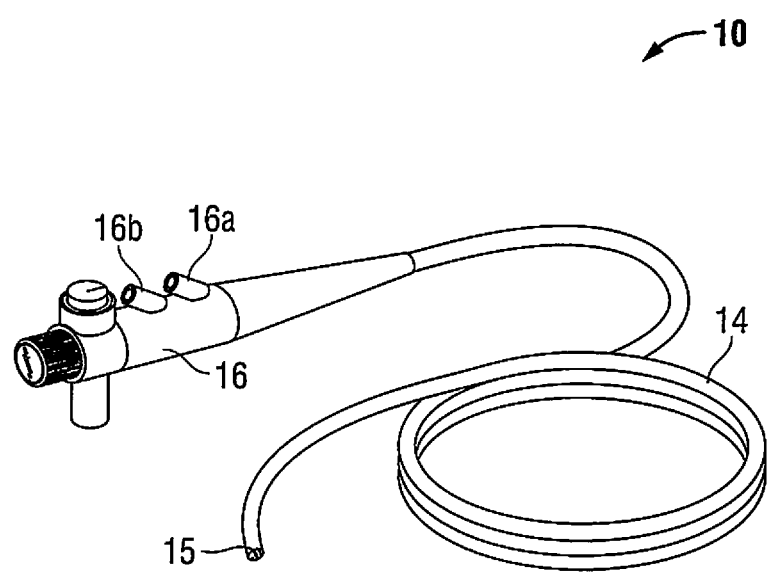
FIG. 1 is a perspective view of a first endoscopic instrument of the present invention configured for transoral insertion into the stomach of a patient.
Figure 2:
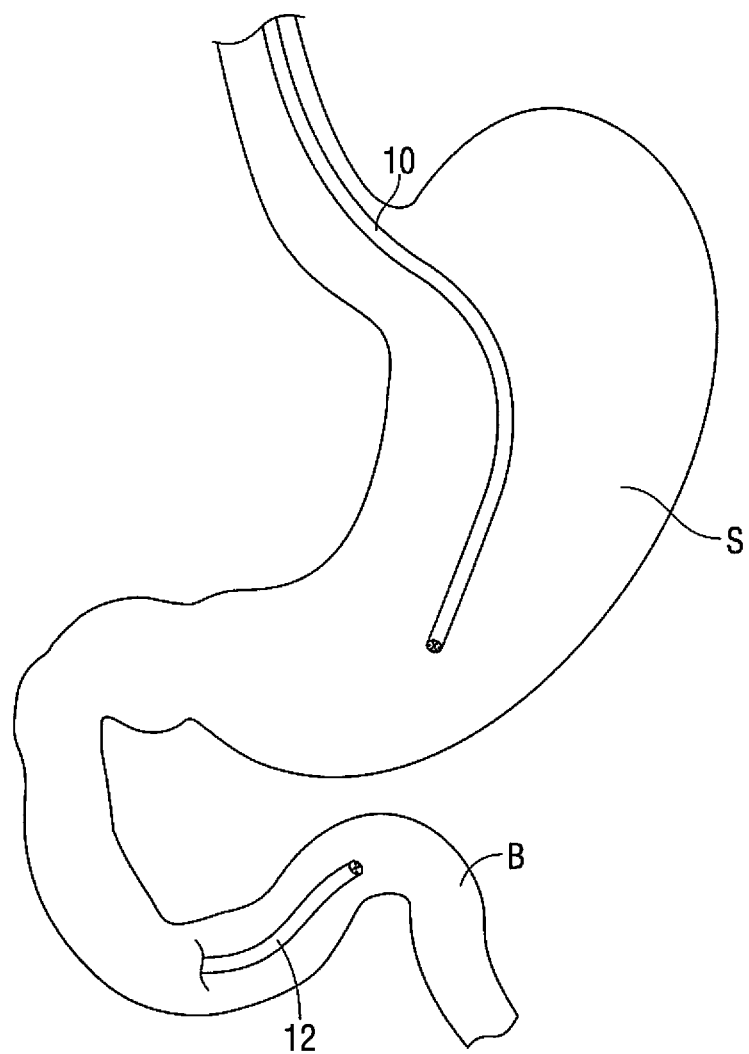
FIG. 2 is a perspective view showing the first endoscopic instrument of FIG. 1 positioned in the stomach and a second endoscopic instrument inserted in the bowel.

Referring now to the drawings wherein like reference numerals identify similar structural features of the apparatus disclosed herein, there is illustrated in FIG. 1 a first endoscopic instrument, designated generally by reference numeral 10. The first endoscopic instrument 10 of the system is configured to be inserted transorally into the stomach S, as shown in FIG. 2. A second endoscopic instrument 12 (FIG. 2) of the system is configured to be inserted into the bowel minimally invasively through a port (not shown). The two instruments 10, 12 deliver first and second magnets, respectively, in performance of a gastric bypass procedure explained in detail below.

As shown in FIG. 1, endoscopic instrument 10 is in the form of an endoscope having visualization capabilities. Endoscopic instrument 10 has a flexible outer tube 14 and a handle 16 with optional access ports 16a, 16b for insertion of instruments, insertion of fluid, and/or aspiration. Instruments inserted through the instrument 10 exit the distal end 15. The flexible tube 14 is dimensioned for insertion through the natural opening of the mouth of the patient and through the esophagus into the patient's stomach to provide a minimally invasive entry into the stomach. In alternate embodiments, the endoscopic instrument 10 can be configured for insertion through an access port for minimally invasive entry into the stomach through a small surgeon-created opening.

Figure 8:
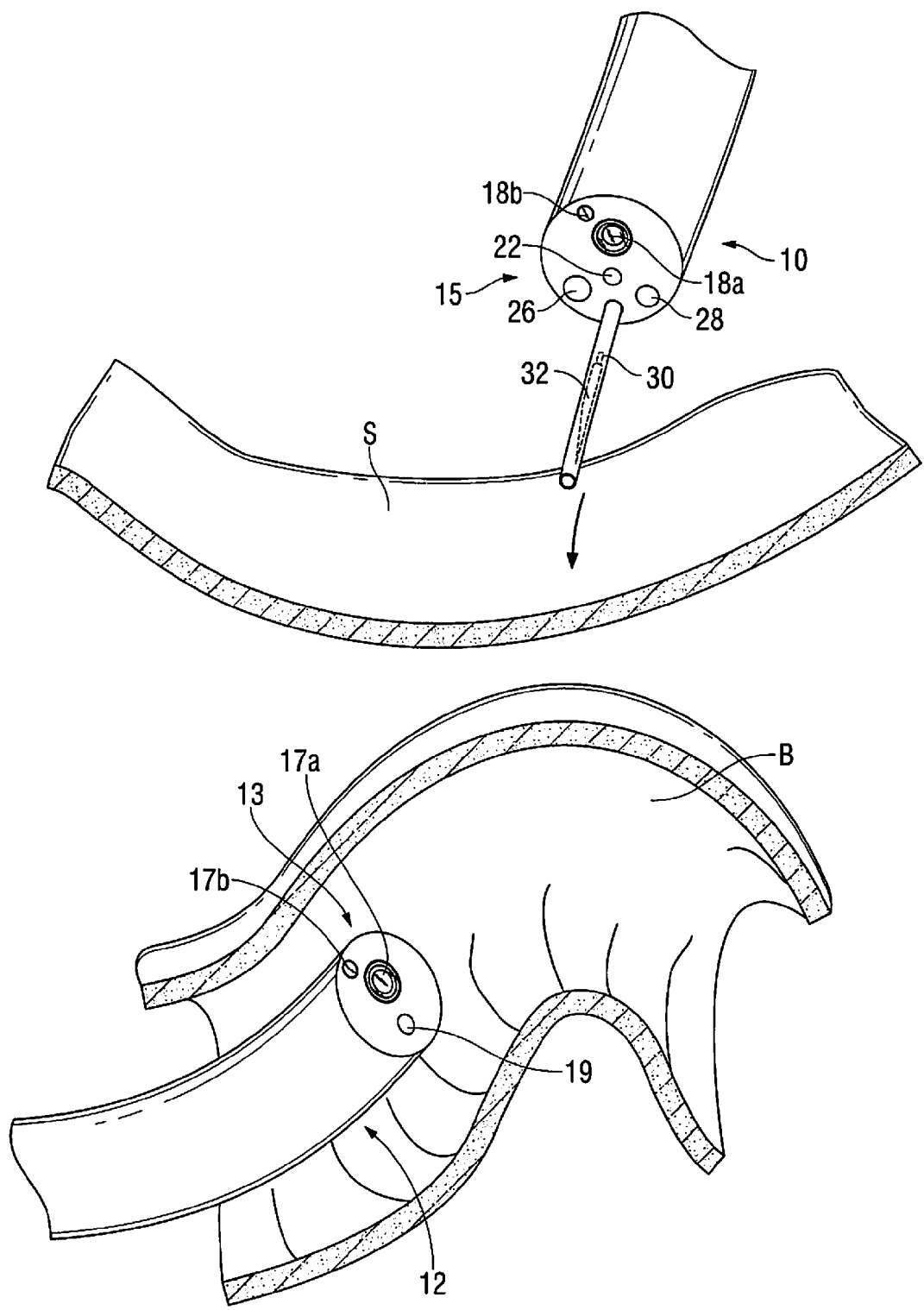

The second endoscopic instrument 12, as shown in FIG. 8, has a distal end 13, imaging lens 17a, an illumination lens or window 17b for the light delivery system, and a lumen 19 to receive a magnet delivery device 49 (FIG. 13) which contains a second magnet described below. The second endoscopic instrument 12 can have flexible tube, handle and access ports as in the first endoscopic instrument 10.

Note the designations of "first" and "second" for the various components and instruments, e.g., endoscopic instruments and magnets, as used herein are merely to identify the separate instruments and components and are not necessarily designated in the order of insertion. For example, the first endoscopic instrument can be inserted before or after the second endoscopic instrument, and the first magnet can be inserted before or after the second magnet.

As used herein, the term "proximal" denotes the portion of the instrument closer to the user and the term "distal" denotes the portion of the instrument further from the user.

Figure 3A:
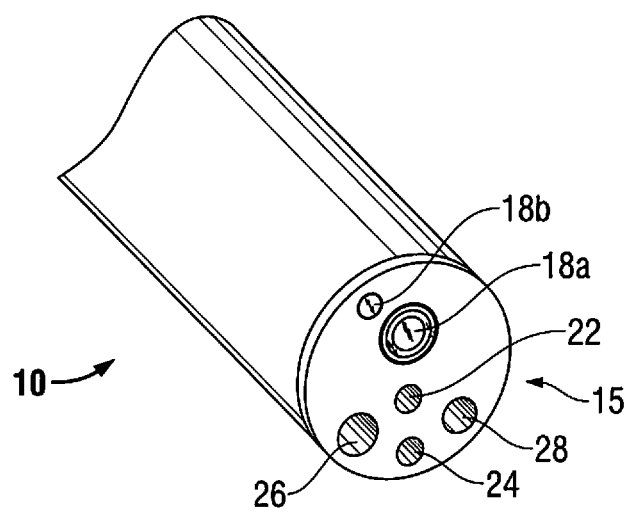
FIG. 3A is a front perspective view of the first endoscopic instrument of FIG. 1.

In the embodiment of FIG. 3A (and FIG. 8), the first endoscopic instrument 10 has four working channels (lumens), an imaging lens 18a for visualization of the surgical site and an illumination lens or window 18b for the light delivery system for illuminating the surgical site. The four working channels or lumens are for the various components of the system which are deployable from the instrument 10 for performing the gastric bypass procedure. More specifically, lumen 22 receives a magnet delivery device 40 for delivering a magnet 42 adjacent the inner stomach wall, lumen 24 receives a sheath 30 for delivering a needle 32 and T-bar 34 for approximating the wall of the stomach and the wall of the bowel, lumen 26 receives a cutting instrument (device) 36 for cutting an opening between the deployed magnet 42 and a second magnet which is deployed in the bowel, and lumen 28 receives a stent sheath 50 for delivery of a stent 52 in the openings in the magnets and through the approximated walls of the stomach and bowel to maintain the opening between the approximated stomach and bowel. The lumens 22, 24, 26, 28 can be of various sizes and the instruments can be inserted through lumens other than the particular lumen designated in FIG. 8, e.g., sheath 30 can be inserted through lumen 28 and stent sheath 50 inserted through lumen 24.

Figure 3B:
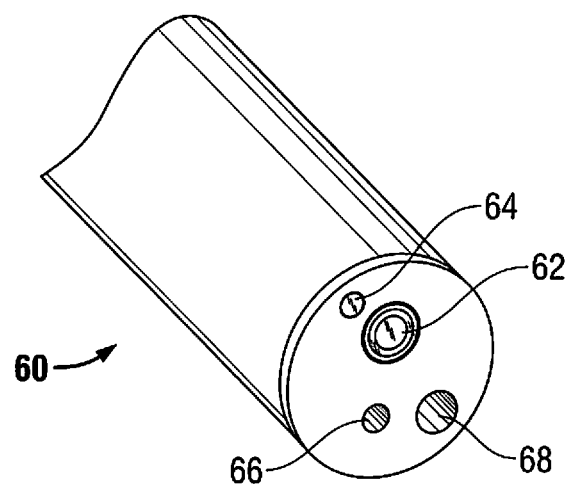
FIG. 3B is a front perspective view of an alternate embodiment of the first endoscopic instrument of the present invention.
Figure 6:
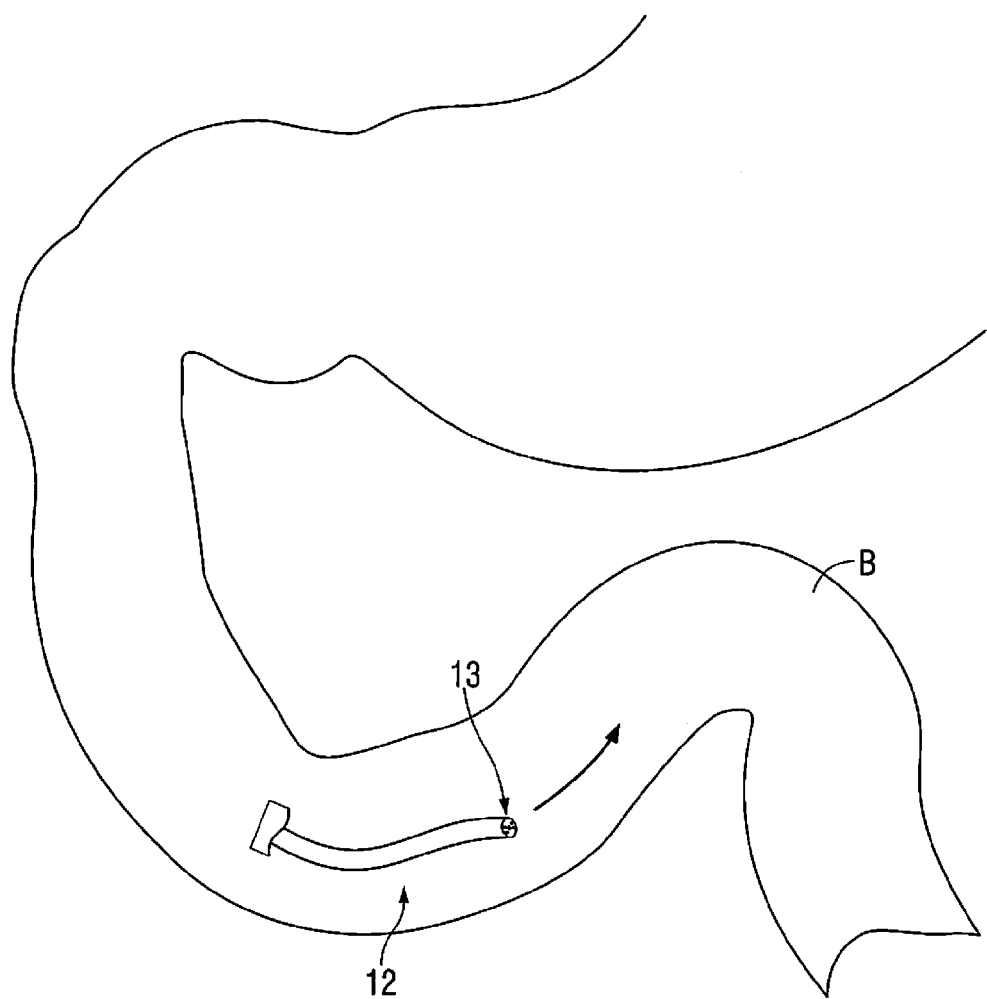

In the alternate embodiment of FIG. 3B, the endoscopic instrument 60 has fewer working channels (lumens), thereby reducing the overall diameter of the instrument 10. In this embodiment, the same channel can be used to deploy several components of the system. For example, endoscopic instrument 60 of this alternate embodiment has an imaging lens 62 and an illumination lens or window 64 for visualizing and illuminating the surgical site as in the endoscopic instrument 10 of FIG. 3A. However, endoscopic instrument 60 has a lumen 66 for the needle 32 and T-bar 34 and a lumen 68 for the magnet delivery device 40 and magnet 42. In this embodiment, the lumen 68 used for magnet delivery can also be used for the cutting device 36, inserted after the magnet delivery device 40 is withdrawn from the lumen after delivery of the magnet 42. The stent delivery device (stent sheath 50) can then be inserted through the lumen 68 after withdrawal of the cutting instrument 36. Note that lumen 66 can alternatively be used for the cutting device and/or stent delivery. As can be appreciated, the embodiment of FIG. 3B enables a smaller diameter endoscope to be utilized since a single lumen can be used for multiple purposes. However, the embodiment of FIG. 3A has the advantages of quicker procedure time and ease of use as the various devices/components can be preloaded in the endoscope working channels so the user does not need to fully withdraw one device and then insert another device through the endoscope working channel as in the embodiment of FIG. 3B. Even if not preloaded, the instrument of FIG. 3A still saves procedural time because one device does not have to be fully removed from the instrument before another device is inserted.

The first magnet 42 is illustrated in FIG. 4. Preferably the magnet 42 is delivered in a substantially linear configuration, maintained in this delivery configuration (position) by a magnet delivery device (sheath) 40 (see FIG. 11). When deployed from the delivery device 40, the magnet 42 returns to a curved placement/configuration for placement at the stomach wall. In the embodiment of FIG. 5A, the magnet 42 returns to a circular, 360 degree shape. In the alternate embodiment of FIG. 5B, the magnet 42' returns from its substantially linear delivery configuration to a C-shaped configuration so that ends 42a and 42b are spaced apart. In either embodiment, the magnet 42, 42' has an opening or space 45, 45' respectively, to receive a cutting device and then a stent as described in more detail below in conjunction with the method of use. Note the magnet 42, 42', can be composed of a shape memory material such as a nickel titanium alloy, e.g., Nitinol, with a curved memorized configuration to which it returns upon deployment, e.g., a memorized position of FIG. 5A or 5B. Other materials are also contemplated.

The second magnet 48 can be the same as the first magnet 42 (or 42') and its variations described above, and made of the same or alternate material as magnet 42 (or 42'). It is contained in the magnet delivery device (sheath) 49 (FIG. 13) in a substantially linear delivery configuration (position) and delivered into the bowel for placement at the bowel wall as described below where it returns to a curved configuration in a similar manner as magnet 42 or 42' shown in FIG. 5A or FIG. 5B.

Figure 7:
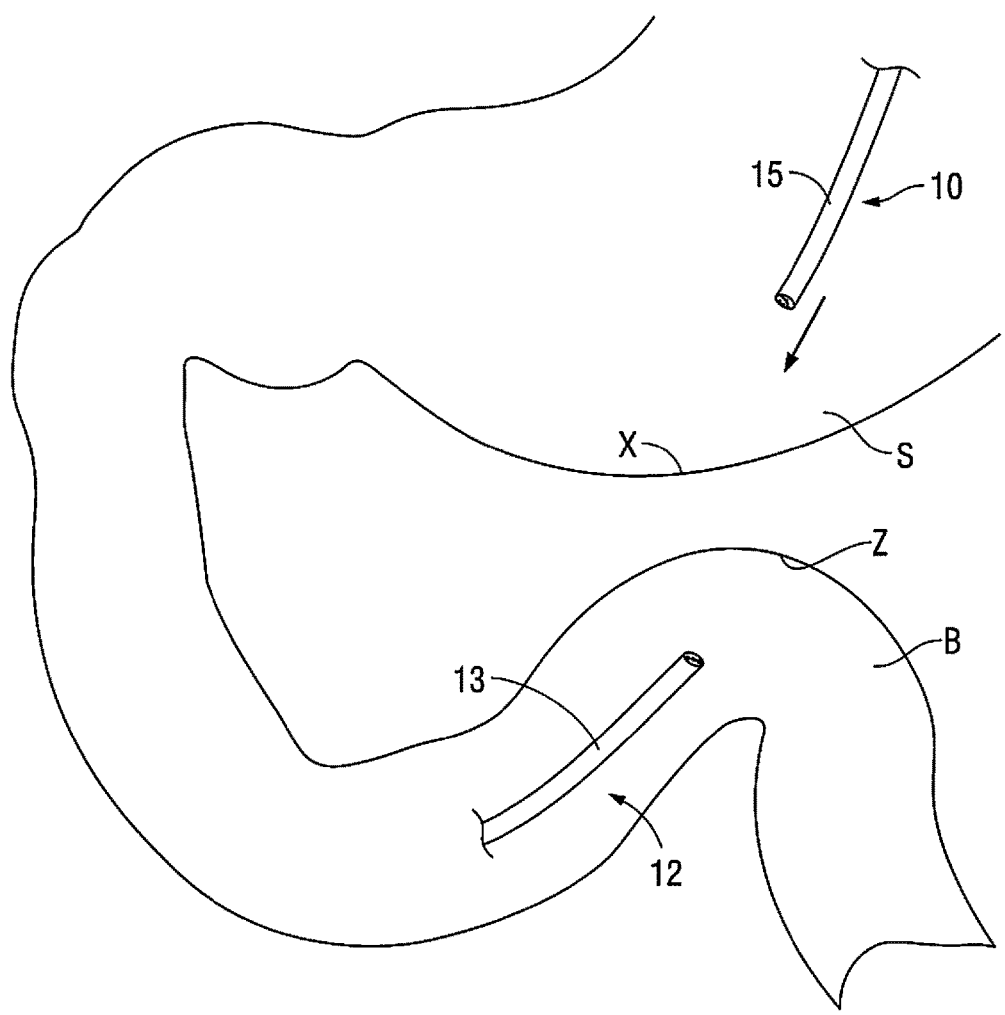

The method of use of the system of the present invention for performing gastric bypass will now be discussed in conjunction with FIGS. 6-20. It should be noted that the system can alternatively be used for other surgical procedures. The first endoscope or endoscopic instrument 10 is inserted transorally into the stomach S so that its distal end 15 is adjacent the stomach wall X as shown in FIG. 7. The second endoscope or endoscopic instrument 12 is inserted through a trocar port into the bowel B with its distal end 13 adjacent the bowel wall Z (FIG. 7). Note the first endoscope 10 does not necessarily need to be inserted before the second endoscope 12, e.g., it could alternatively be inserted after the second endoscope 12 is inserted into the bowel B. Additionally, the first and second endoscopes 10, 12 can be inserted via other ways into the stomach and bowel, respectively.

Figure 9:
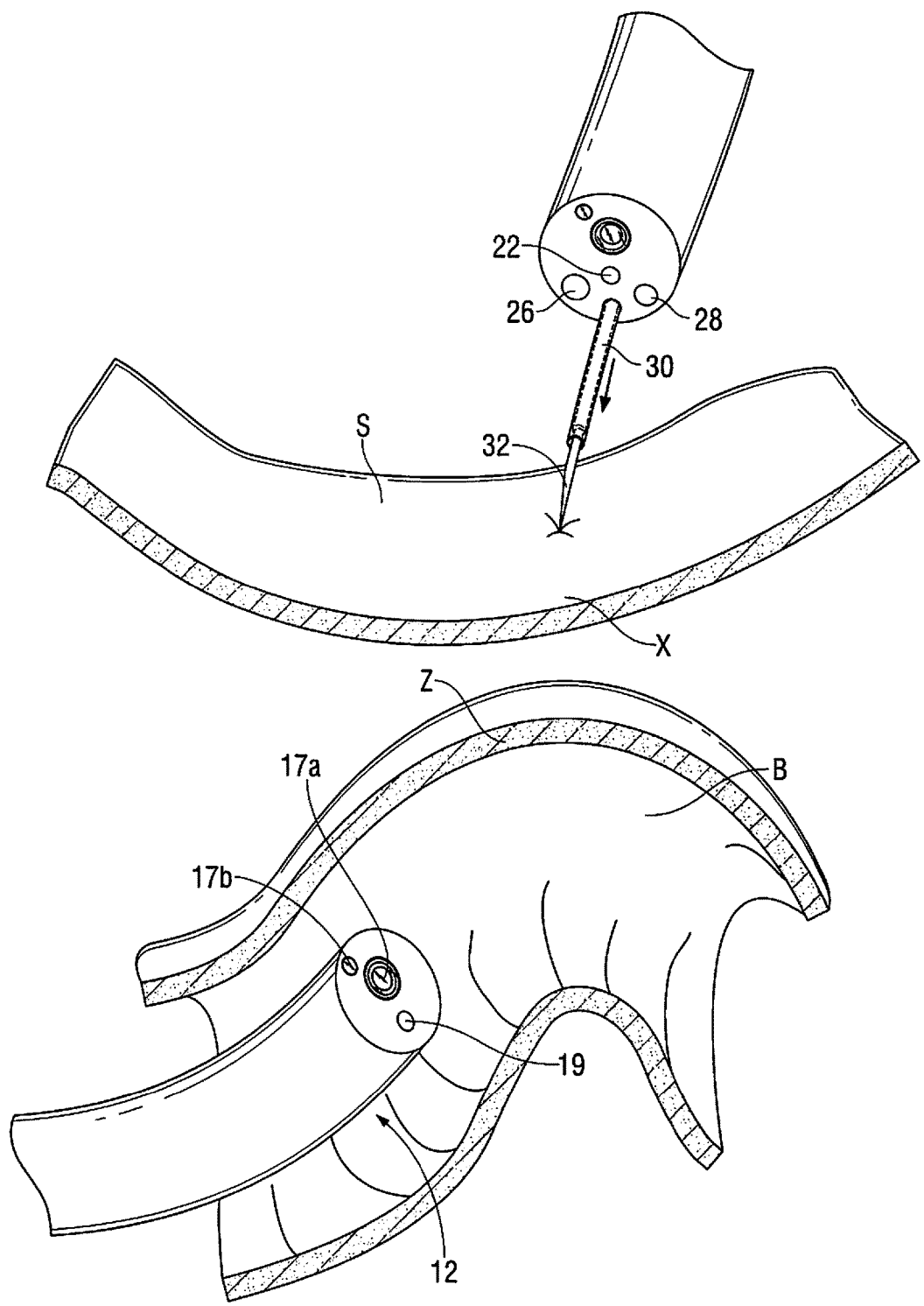
Figure 10:
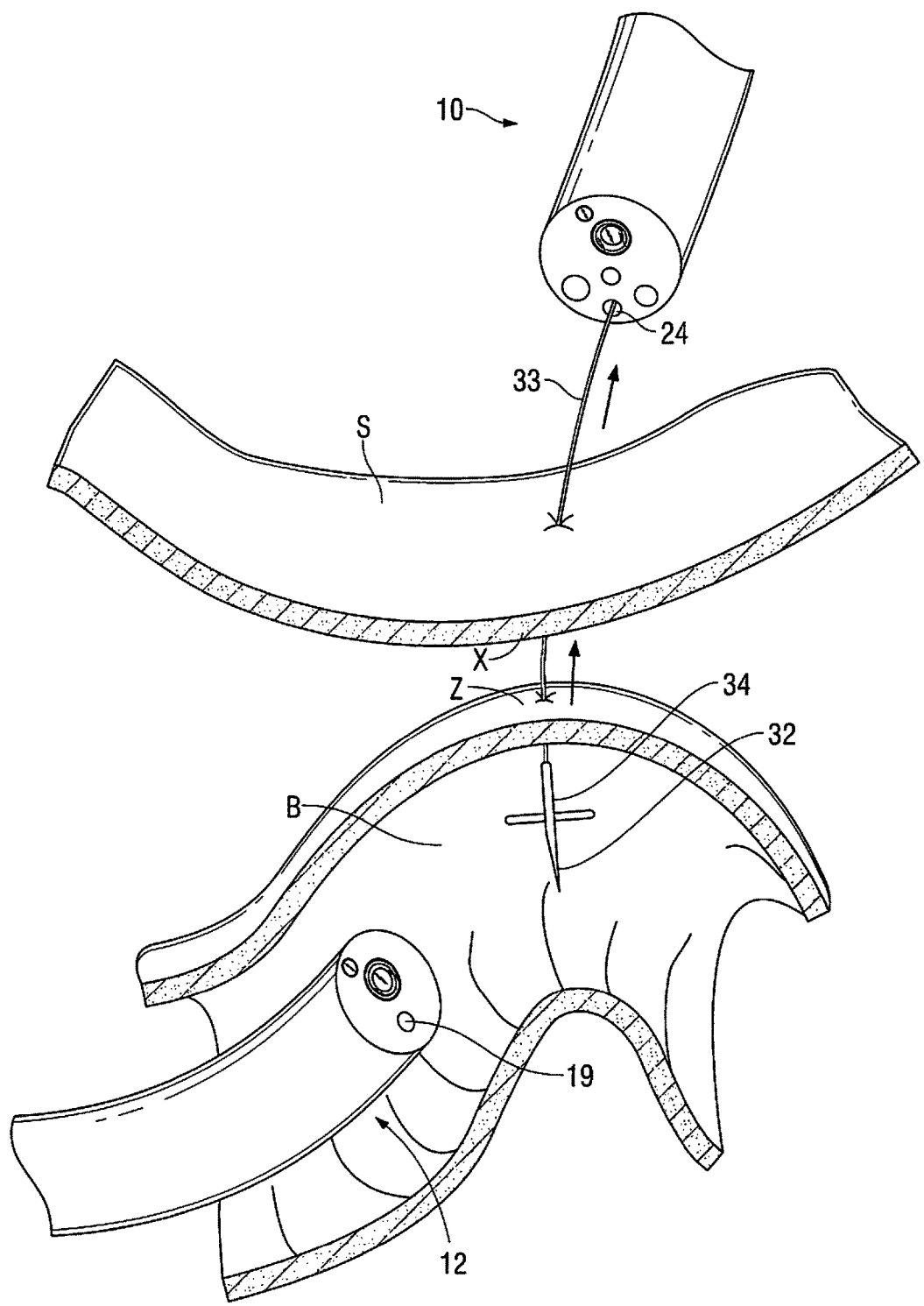
Figure 11:
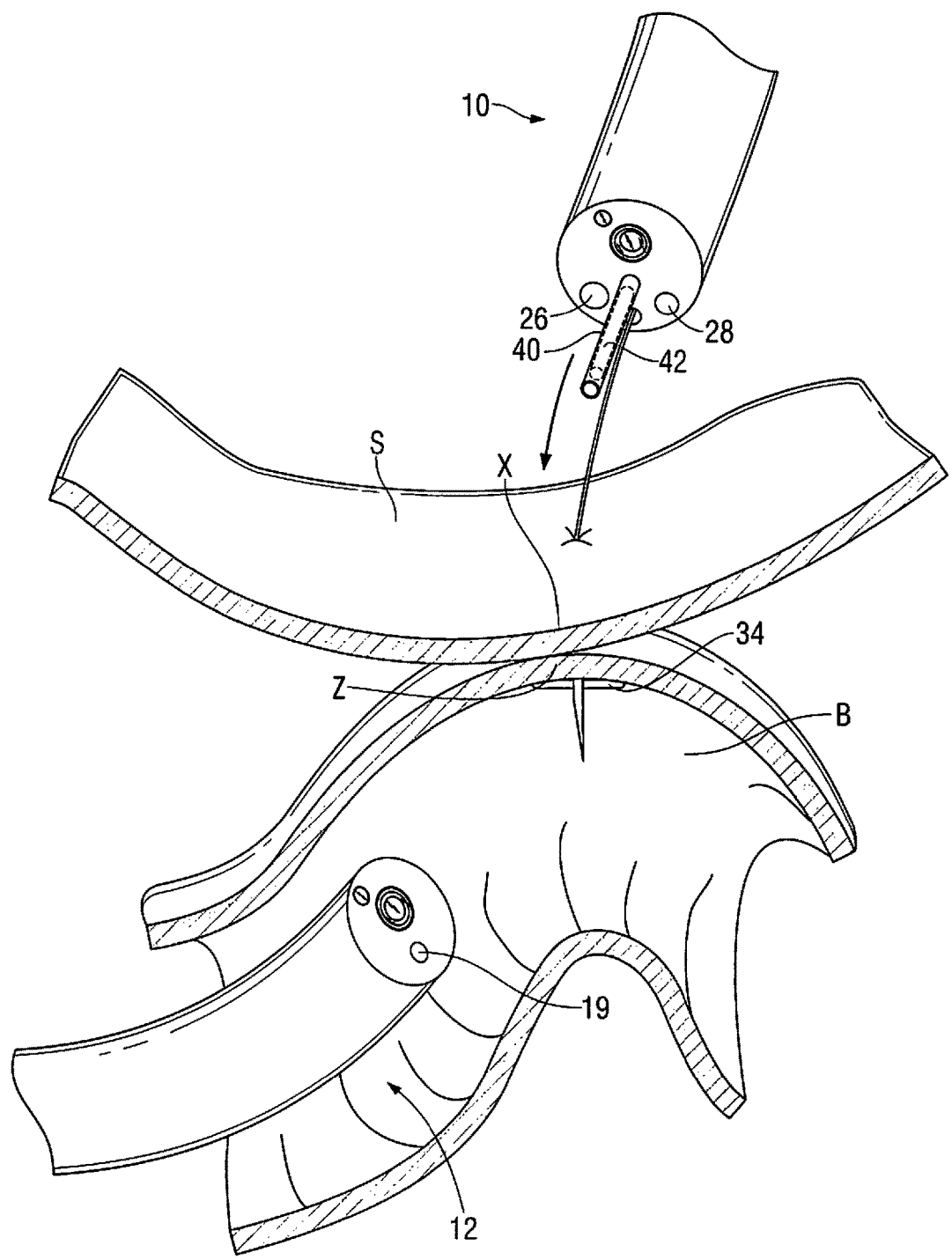
Figure 12:
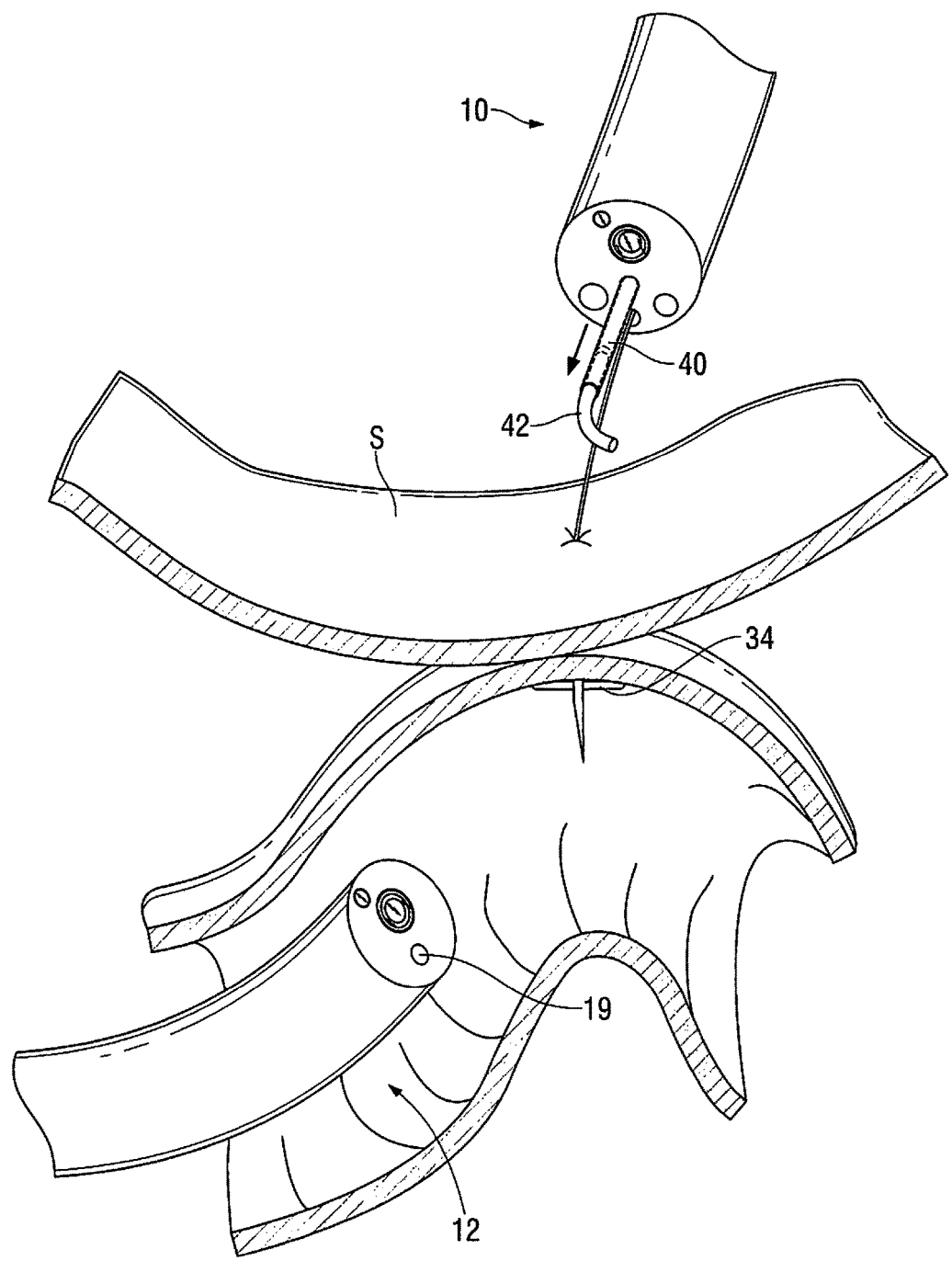
Figure 13:
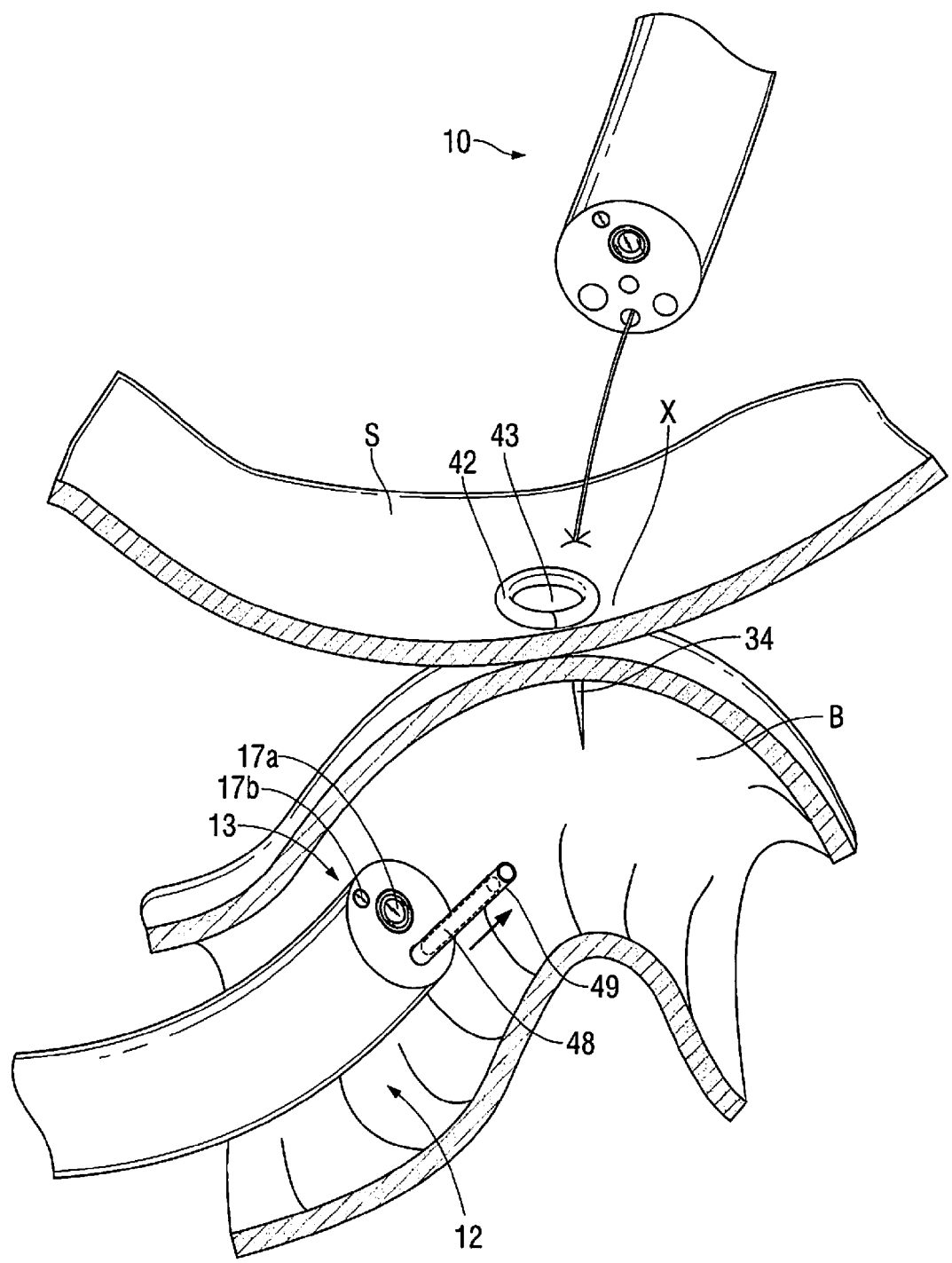

Once positioned in the stomach S, a needle and T-bar delivery sheath 30 is advanced from lumen 24 of the endoscope 10 as shown in FIG. 8. The needle 32, which carries the T-bar 34, is advanced from sheath 30 by a pusher (not shown) to form a puncture through the wall X of the stomach S and the wall Z of the bowel to advance the T-bar 34 into the bowel B as shown in FIGS. 9 and 10. Sheath 30 can then be retracted or a flexible T-bar connector 33 pulled proximally to pull T-bar 34 proximally to engage the inner side of wall Z of the bowel B and to move the wall Z toward the stomach wall X to approximate the bowel B and stomach S (FIG. 11). The sheath 30 can be retracted within lumen 24. Magnet delivery sheath 40 is then advanced from the lumen 22 of the endoscope 10 (FIG. 11), and a pusher (not shown) within the delivery sheath 40 advances the magnet 42 from the sheath 40. The magnet 42 as shown is retained in a substantially linear delivery position along a longitudinal axis of the delivery sheath 40 for insertion. When the magnet 42 is exposed, it resumes its shape memory position as shown in FIGS. 12 and 13, and when fully exposed assumes the curved circular configuration of FIGS. 13 and 5A (or alternatively the C-shape as in FIG. 5B), placed to rest against the internal side of the stomach wall X. As shown, the circular shape of the magnet 42 has an opening 43.

Figure 14:
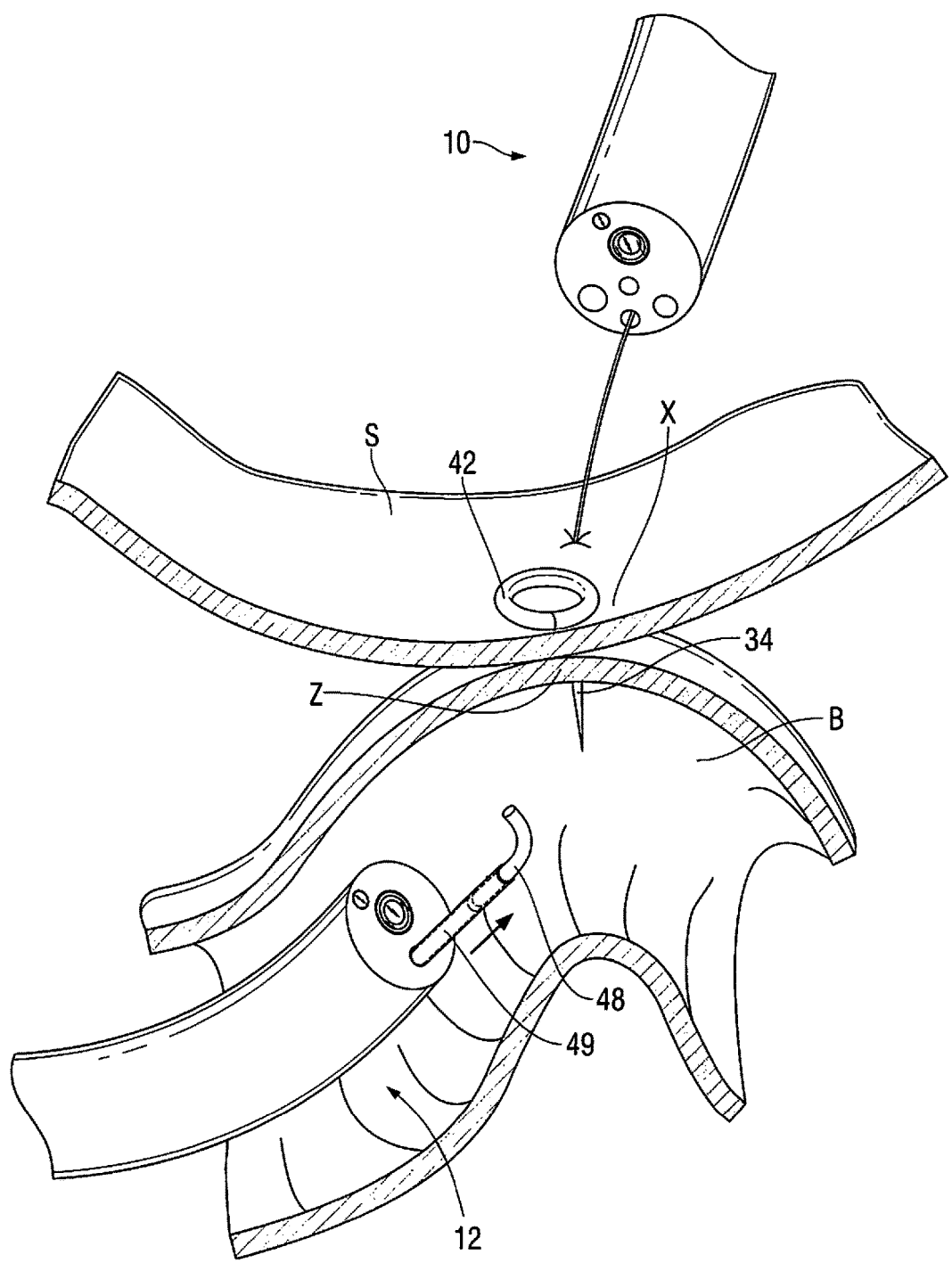
Figure 15:
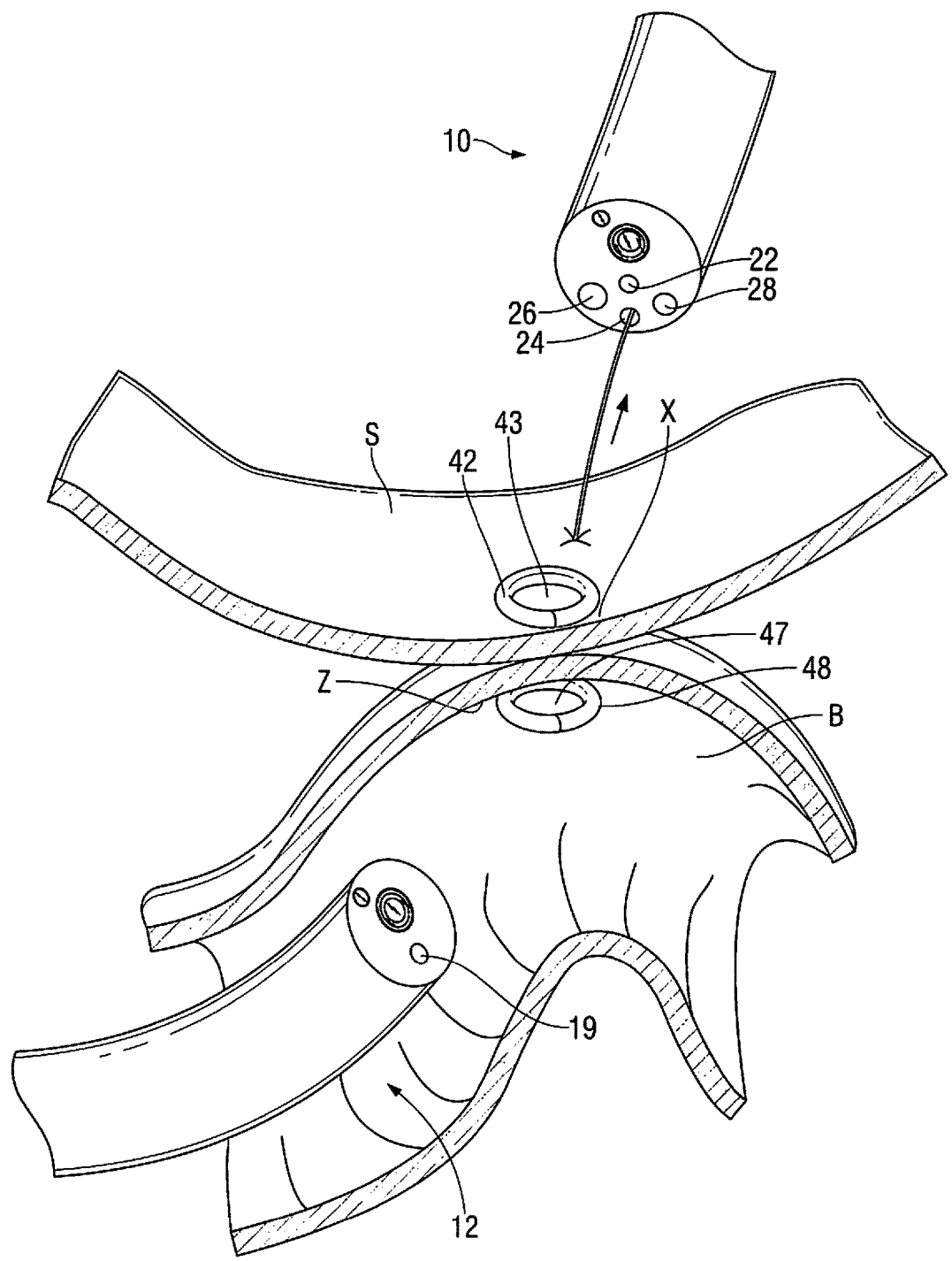

Magnet delivery sheath 49 is then advanced from the lumen 19 of the endoscope 12 (FIG. 13), and a pusher (not shown) within the delivery sheath 49 advances the magnet 48 from the sheath 49. The magnet 42 is retained in a substantially linear delivery position along a longitudinal axis of the delivery sheath 49. When the magnet 48 is exposed, it resumes its shape memory position as shown in FIGS. 14 and 15, and when fully exposed assumes the curved circular configuration of FIGS. 15 and 5A (or alternatively the C-shape like magnet 42' of FIG. 5B), placed to rest against the internal side of the bowel wall Z. As shown, the circular shape of the magnet 48 has an opening 47. The attraction forces of the two magnets 42 and 48 maintain the stomach and bowel walls in approximation. Note the T-bar 34 can be removed once the magnets 42 and 48 are in position to maintain the stomach and bowel walls in approximation due to the magnetic attraction forces.

Figure 16:
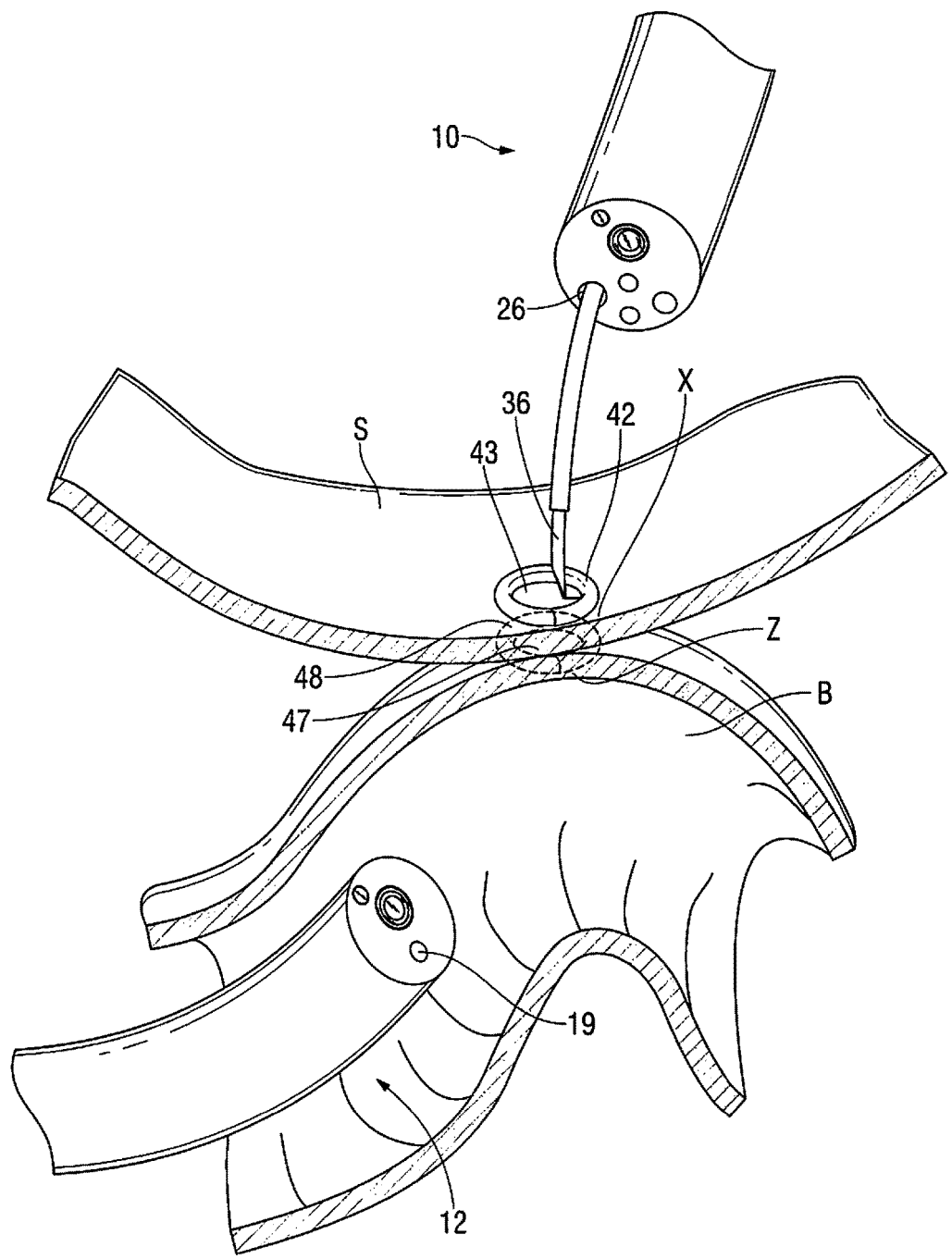
Figure 17:
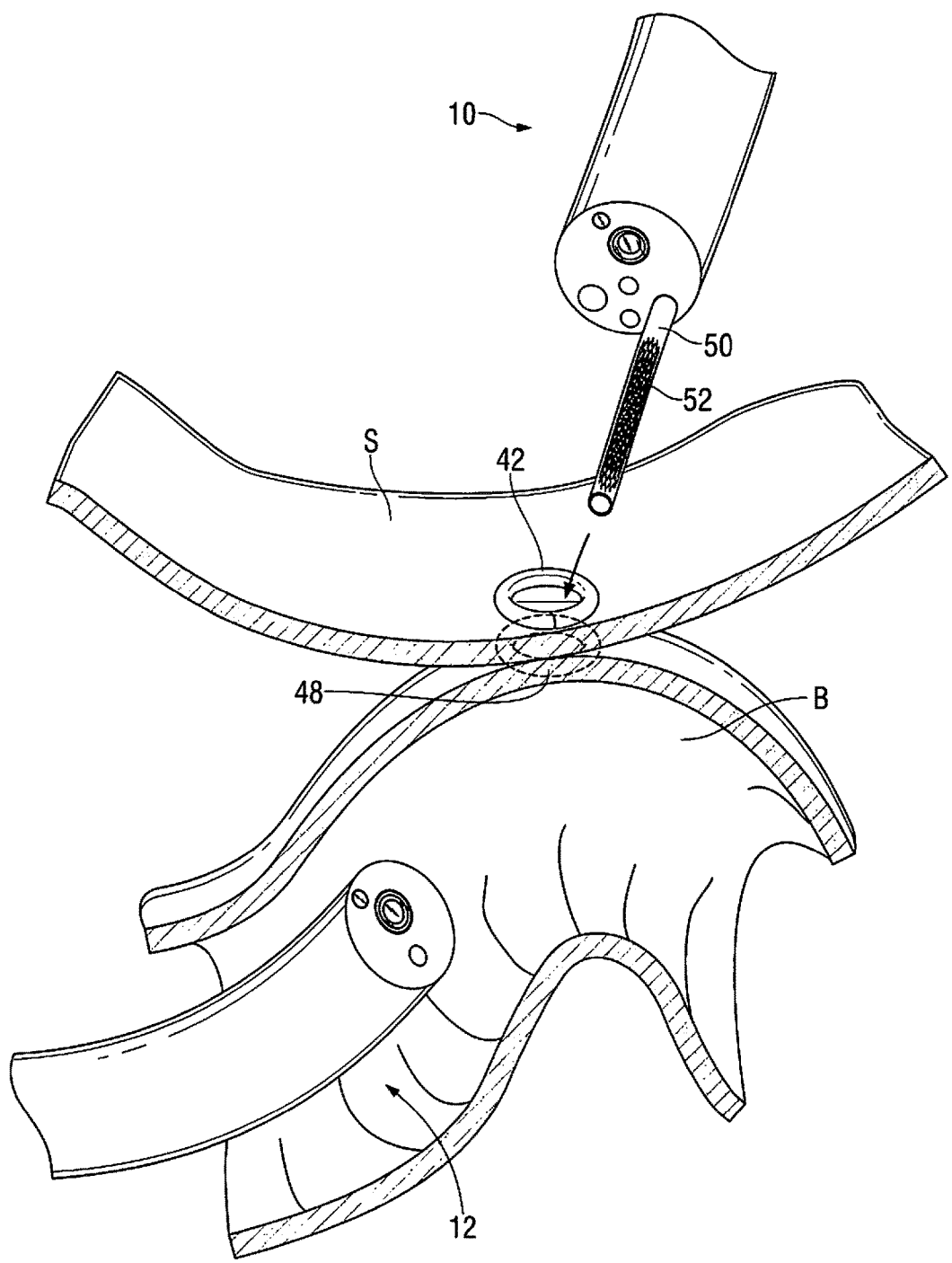
Figure 18:
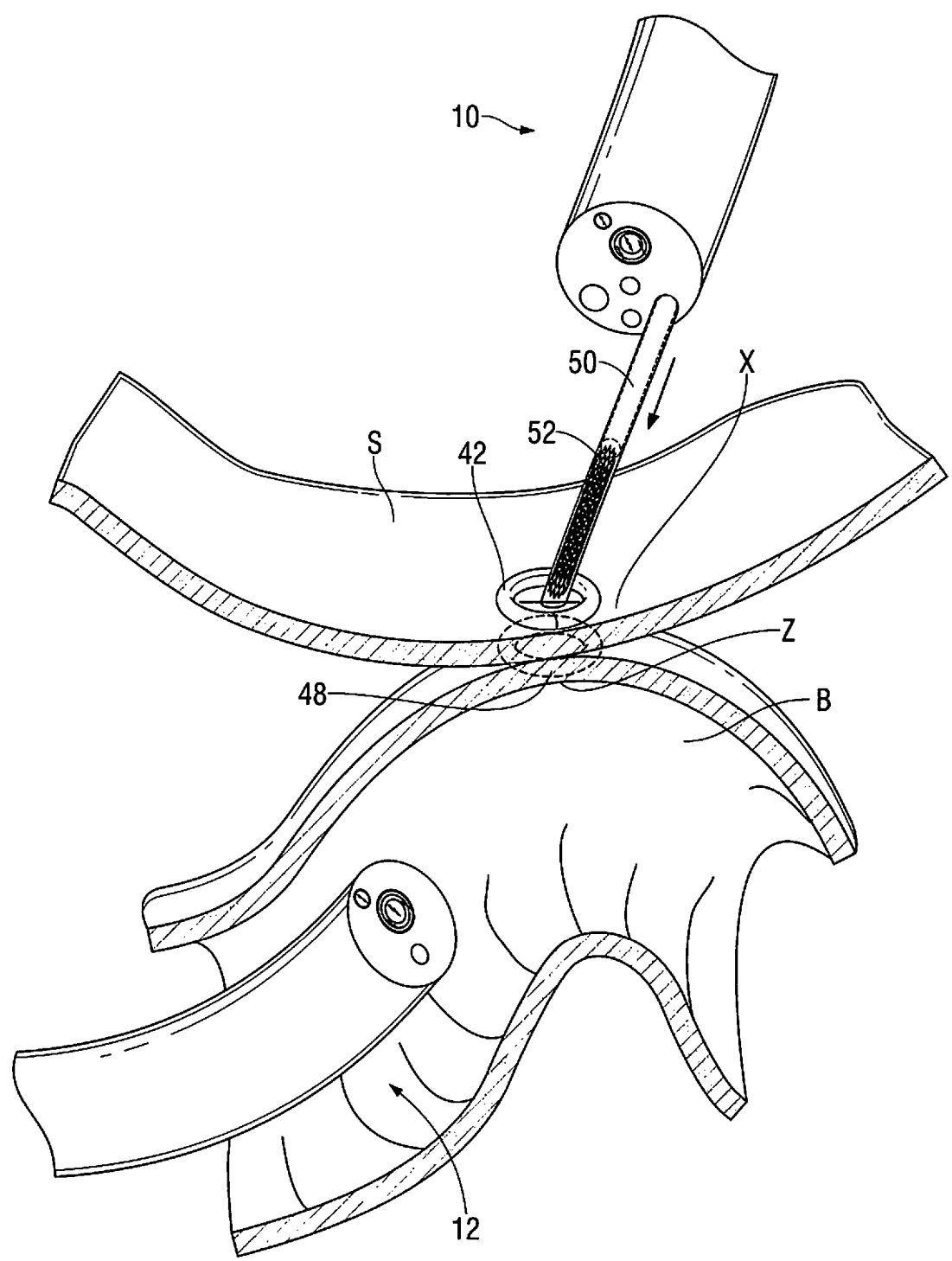

Once the magnets 42, 48 are in position, cutting instrument 36 is advanced from the lumen 26 of the endoscope 10 (FIG. 16). The cutting instrument 36 is advanced through the openings 43 and 47 of magnets 42, 48, respectively, to make an incision through the stomach wall X and bowel wall Z.

Figure 19:
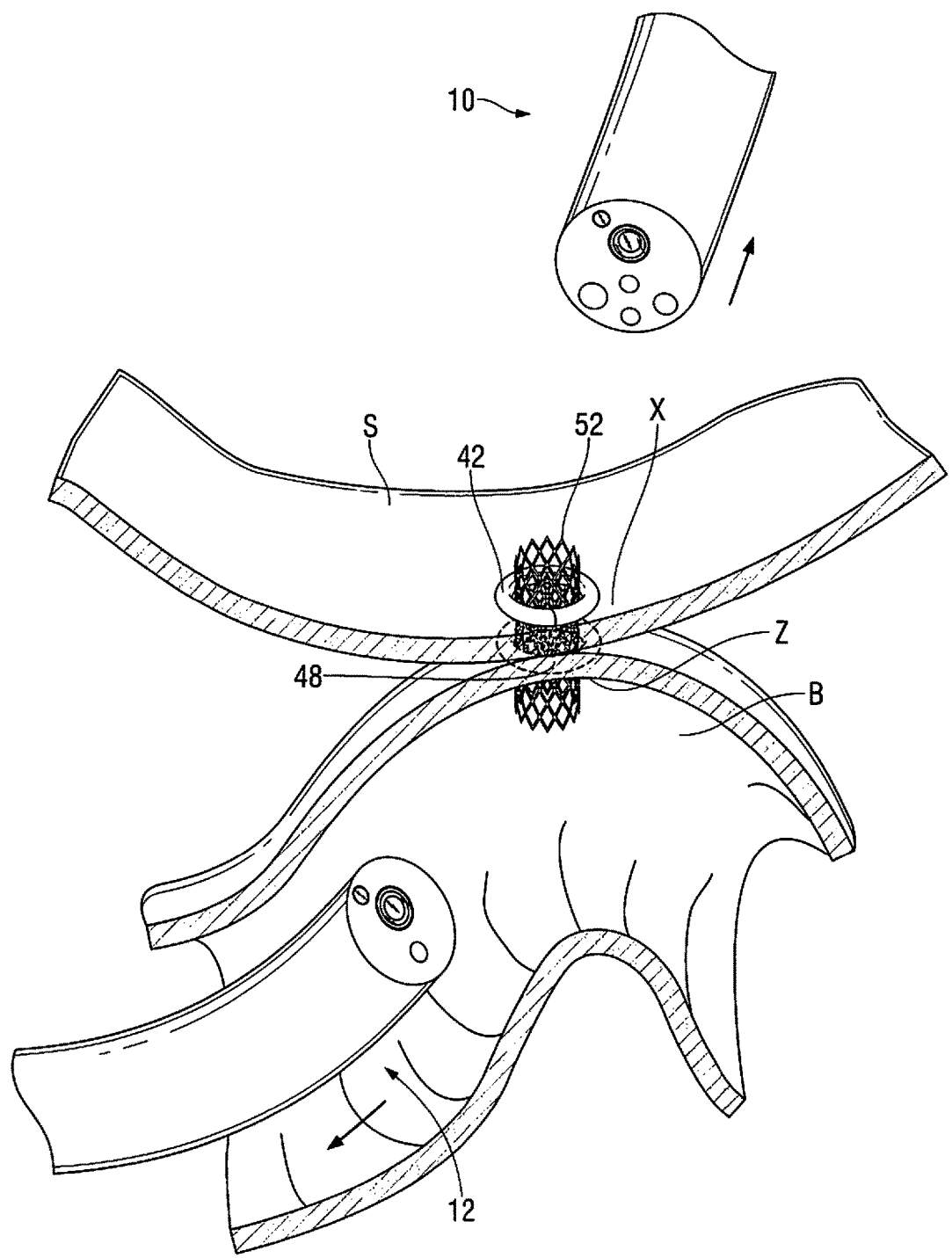
Figure 20:
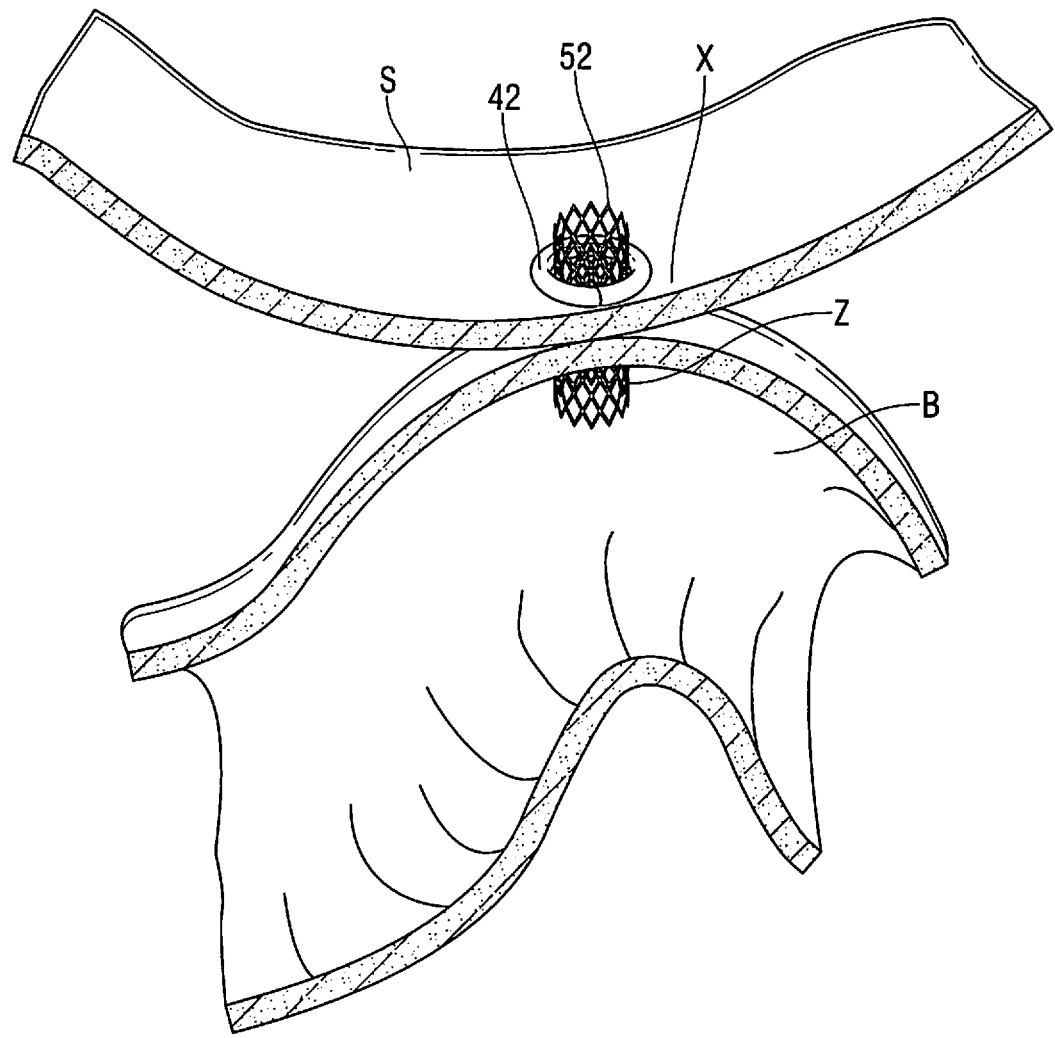

The cutting instrument 36 is then withdrawn, and stent sheath 50 (FIGS. 17 and 18) is advanced from lumen 28 of endoscope 10. A stent 52 is contained within the stent sheath 50 in a reduced diameter collapsed position. The sheath 50 is inserted through the incision through the stomach wall X, bowel wall Z and into the bowel B. The sheath 50 is then withdrawn, or the stent 52 exposed from the sheath 50, allowing the stent 52 to expand to a larger diameter expanded second position within openings 43, 47 of magnets 42, 48, and leaving the stent 52 in position to maintain the opening between the stomach S and bowel B as shown in FIG. 19. The endoscopic instruments (or endoscopes) 10, 12 can then be withdrawn. FIG. 20 shows the stent 52 in position with the endoscopes 10 and 12 removed from the body. A portion of the stomach is then closed off such as by a stapling instrument (not shown) or suturing. With the stent 52 in the position of FIG. 20, contents pass from the stomach into the bowel B through the openings in the stomach wall X and bowel Z.

The procedure provides immediate results as the bypass opening is formed during the procedure. The surgeon can also see the opening before the patient is released due to the visualization provided by the endoscopes, thereby increasing efficacy of the procedure.

Figure 21:
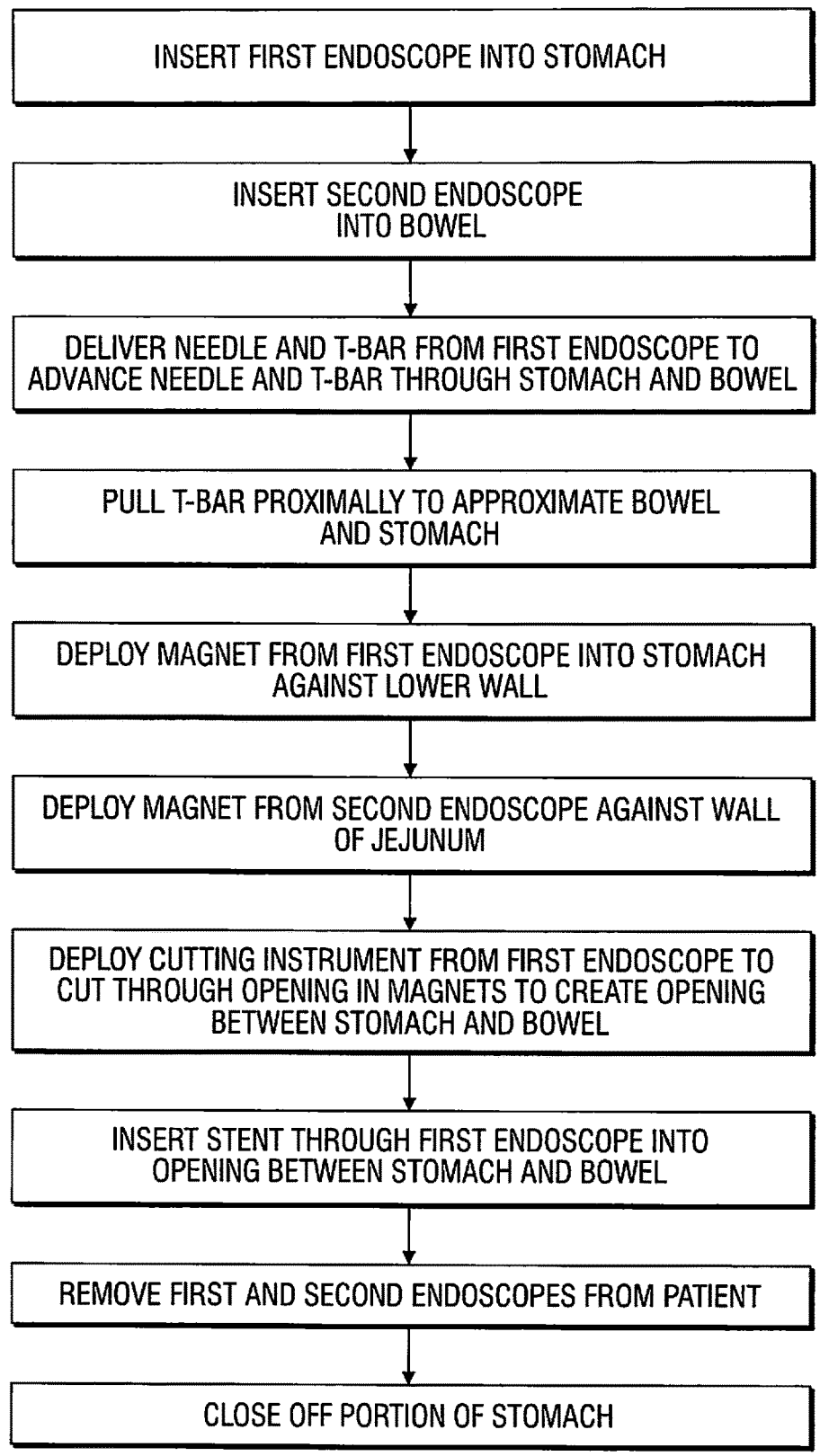
FIG. 21 is a flow chart showing the procedural steps of the system of the present invention.

FIG. 21 provides a flow chart setting forth the method steps of the present invention. The steps are as follows: insert a first endoscope (or endoscopic instrument) into the stomach, insert a second endoscope (or endoscopic instrument) into a bowel (although the second endoscope could alternatively be inserted before the first endoscope), deliver a needle and T-bar from the first endoscope to advance the needle and T-bar though the stomach and bowel, pull the T-bar proximally to approximate the bowel and stomach, deploy a first magnet from the first endoscope into the stomach against the lower wall, deploy a second magnet from the second endoscope against a wall of the jejunum (although the second magnet could alternatively be placed (deployed) before the first magnet), deploy a cutting instrument from the first endoscope to cut through the opening in the magnets to create an opening between the stomach and bowel, deliver (insert) a stent from the first endoscope into the opening between the stomach and bowel (through the openings in the magnets), remove the first and second endoscopes from the patient, and close off a portion of the stomach. Note the T-bar can be removed after placement of the first and second magnets.

Note the magnets can be removed after a period of time if desired.

Although the apparatus and method of the subject invention have been described with respect to preferred embodiments, those skilled in the art will readily appreciate that changes and modifications may be made thereto without departing from the spirit and scope of the present invention as defined by the appended claims.

What is claimed is:

1. A method for treating obesity comprising the steps of:
   inserting first and second endoscopes, the first endoscope inserted into a stomach of the patient and the second endoscope inserted into a bowel of a patient;
   inserting an approximating device and approximating the stomach and bowel;
   deploying a first magnet in the stomach and a second magnet in the bowel, the first magnet having a curved configuration defining a first space and the second magnet having a curved configuration defining a second space;
   inserting a cutting tool through the first and second spaces to penetrate a wall of the stomach and a wall of the bowel to create an opening between the stomach and bowel,
   after placement of the first and second magnets, inserting a stent delivery sheath through the first and second spaces of the first and second magnets; and
   after insertion of the stent delivery sheath, deploying a stent from the stent delivery sheath to enable expansion of the stent within the first and second spaces of the first and second magnets and placement in the opening between the stomach and bowel;
   wherein the steps of inserting the approximating device, deploying the first and second magnets, inserting the cutting tool and inserting the stent delivery sheath are all performed through lumens in respective endoscopes without removing the endoscopes from the body between performance of the steps.

2. The method of claim 1, wherein the step of inserting the first endoscope into the stomach includes advancing the first endoscope transorally into the stomach.

3. The method of claim 1, further comprising the step of inserting a T-bar through a wall of the stomach and a wall of the bowel and the step of approximating the stomach and bowel includes the step of pulling the T-bar proximally.

4. The method of claim 1, wherein the first magnet is deployed from the first endoscope and the second magnet is deployed from the second endoscope, and the stent delivery sheath is inserted through a lumen in the first endoscope.

5. The method of claim 1, wherein the first magnet is retained in the first endoscope in a substantially linear position and the first magnet moves to the curved configuration after deployment from the first endoscope.

6. The method of claim 5, wherein the second magnet is retained in the second endoscope in a substantially linear position and the second magnet moves to the curved configuration after deployment from the second endoscope.

7. The method of claim 1, wherein the first endoscope has a first channel to receive the first magnet and a second channel to receive a device for approximating the stomach and bowel, and the step of deploying the first magnet advances the first magnet from the first channel.

8. The method of claim 7, wherein the first endoscope has a third channel to receive the stent and the step of deploying the stent within the first and second spaces includes the step of advancing the stent from the third channel.

9. The method of claim 1, further comprising the step of removing the first and second endoscopes and closing off a portion of the stomach.

10. A system for treating obesity comprising:
    a first instrument containing a first magnet therein, the first instrument insertable into a stomach of a patient and the first magnet deployable into the stomach of the patient, the first magnet having a first space;
    a second instrument containing a second magnet therein, the second instrument insertable into a bowel of the patient and the second magnet deployable into the bowel of the patient, the second magnet having a second space;
    a tissue approximating device insertable through the first instrument; and
    a stent delivery sheath positioned in the first instrument, the stent delivery sheath containing a stent therein, the stent delivery sheath insertable into the first and second spaces of the first and second magnets after deployment of the first and second magnets and the stent insertable into the first and second spaces of the first and second magnets to maintain an opening formed between the stomach and bowel, the first magnet, the tissue approximating device, the stent delivery sheath and the stent inserted through the first instrument without removing the first instrument from the body.

11. The system of claim 10, wherein the first magnet is retained in the first instrument in a substantially linear position in the delivery configuration and has a curved placement configuration after deployment from the first instrument.

12. The system of claim 11, wherein the second magnet is retained in the second instrument in a substantially linear position in the delivery configuration and has a curved placement configuration after deployment from the second instrument.

13. The system of claim 10, wherein the second magnet is retained in the second instrument in a substantially linear position in the delivery configuration and has a curved placement configuration when deployed from the second instrument.

14. The system of claim 10, wherein the stent delivery sheath is positioned in a lumen of the first instrument, the stent has a first collapsed configuration when positioned in the first instrument within the stent delivery sheath and an expanded second position after exposure from the stent delivery sheath and first instrument.

15. The system of claim 10, wherein the first instrument has a first channel to receive the first magnet and a second channel to receive a device for approximating the stomach and bowel.

16. The system of claim 10, further comprising a T-bar and T-bar delivery instrument positionable within the first instrument.

17. The system of claim 16, further comprising a cutting instrument insertable through the first instrument and through the first and second spaces of the first and second magnets.

* * * * *